United States Patent
Sprenger

(10) Patent No.: US 9,943,556 B2
(45) Date of Patent: Apr. 17, 2018

(54) SYNBIOTIC MIXTURE

(71) Applicant: NESTEC S.A., Vevey (CH)

(72) Inventor: Norbert Sprenger, Savigny (CH)

(73) Assignee: Nestec S.A., Vevey (CH)

( * ) Notice: Subject to any disclaimer, the term of this patent is extended or adjusted under 35 U.S.C. 154(b) by 36 days.

(21) Appl. No.: 14/978,064

(22) Filed: Dec. 22, 2015

(65) Prior Publication Data

US 2016/0106788 A1 Apr. 21, 2016

Related U.S. Application Data

(62) Division of application No. 13/963,581, filed on Aug. 9, 2013, now Pat. No. 9,254,303, which is a division of application No. 12/922,377, filed as application No. PCT/EP2009/052166 on Feb. 24, 2009, now Pat. No. 8,961,953.

(30) Foreign Application Priority Data

Mar. 14, 2008 (EP) .................................... 08152765

(51) Int. Cl.
| | |
|---|---|
| C12P 13/02 | (2006.01) |
| A61K 35/747 | (2015.01) |
| A61K 31/702 | (2006.01) |
| A61K 31/7016 | (2006.01) |
| A23L 33/00 | (2016.01) |
| A23L 33/10 | (2016.01) |
| A23L 33/135 | (2016.01) |
| A23L 33/21 | (2016.01) |

(52) U.S. Cl.
CPC ............ *A61K 35/747* (2013.01); *A23L 33/10* (2016.08); *A23L 33/135* (2016.08); *A23L 33/21* (2016.08); *A23L 33/40* (2016.08); *A61K 31/702* (2013.01); *A61K 31/7016* (2013.01); *A23V 2002/00* (2013.01); *A23Y 2220/73* (2013.01)

(58) Field of Classification Search
None
See application file for complete search history.

(56) References Cited

U.S. PATENT DOCUMENTS

| | | |
|---|---|---|
| 5,288,637 A | 2/1994 | Stephen |
| 5,578,302 A | 11/1996 | Brassart et al. |
| 2006/0014717 A1 | 1/2006 | Angrostrom et al. |
| 2007/0274983 A1* | 11/2007 | Kluijtmans ............ A23L 33/21 424/130.1 |
| 2009/0041736 A1 | 2/2009 | Sprenger et al. |

FOREIGN PATENT DOCUMENTS

| | | |
|---|---|---|
| EP | 0199535 | 10/1986 |
| EP | 577903 | 1/1994 |
| EP | 0768375 | 4/1997 |
| EP | 1629850 | 3/2006 |
| EP | 1776877 | 4/2007 |
| WO | 9700078 | 1/1997 |
| WO | 9843494 | 10/1998 |
| WO | 0053200 | 9/2000 |
| WO | 0119960 | 3/2001 |
| WO | 03002127 | 1/2003 |
| WO | 2007105945 | 9/2007 |
| WO | WO 2007101675 A1 | 9/2007 |
| WO | 2060257 | 5/2009 |

OTHER PUBLICATIONS

Rovers et al. Lancet (2004) 363: 465-473.*
Rennie et al. Clin. Infect. Diseases (2005) 41 (Suppl 4): 5234-5238.*
Heikkinen et al. Lancet (2003) 361: 51-59.*
Shoaf et al.,"Prebiotic Galactooligosaccharides Reduce Adherence of Enterophathogenic *Escherichia coli* to Tissue Culture Cells," Infection and Immunity American Society for Microbiology (Dec. 2006) pp. 6920-6928.
Canani et al., "Probiotics for treatment of acute diarrhoea in children: randomised clinical trial of five different preparations," BMJ/Online First/bmj.com pp. 1-6.
Salminen et al., Probiotics: how should they be defined: Trends in Food Science & Technology, vol. 10 (1999), pp.
Thompkinson et al. "Aspects of Infant Food Formulation," Institute of Food Technologists, vol. 6. (2007), pp. 79-102.
Prieto "A Research and Development Program for the Production and Use of Recombinant Oligosaccharides; LNnT, from Concept to Clinical Testing" Annual Conference of the Society for Glycobiology, p. 933, XP008089210.

* cited by examiner

*Primary Examiner* — Susan M Hanley
(74) *Attorney, Agent, or Firm* — K&L Gates LLP

(57) ABSTRACT

A preparation includes N-acetyl-lactosamine and/or an oligosaccharide containing N-acetyl-lactosamine and a probiotic *Lactobacillus* sp. In other aspects, a nutritional composition includes such a preparation, and the preparation is used in the prevention and treatment of pathogenic infections of the gastro-intestinal and upper respiratory tracts.

10 Claims, No Drawings

SYNBIOTIC MIXTURE

CROSS REFERENCE TO RELATED APPLICATIONS

The present application is a divisional of U.S. application Ser. No. 13/963,581 filed Aug. 9, 2013, which is a divisional application of U.S. application Ser. No. 12/922,377 filed Sep. 13, 2010, which is a National Stage of International Application No. PCT/EP2009/052166 filed Feb. 24, 2009, which claims priority to European Patent Application No. 08152765.7 filed Mar. 14, 2008, the entire contents of which are incorporated herein by reference.

FIELD

This invention relates to a preparation comprising a probiotic and a prebiotic oligosaccharide which is specifically designed to enhance the efficacy of the probiotic, to food products comprising said preparation and to uses of the preparation.

BACKGROUND

Mother's milk is recommended for all infants. However, in some cases breast feeding is inadequate or unsuccessful for medical reasons or the mother chooses not to breast feed. Infant formulas have been developed for these situations.

In the recent past, certain strains of bacteria have attracted considerable attention because they have been found to exhibit valuable properties for man if ingested. In particular, specific strains of the genera *Lactobacilli* and *Bifidobacteria* have been found to be able to colonise the intestinal mucosa, to reduce the capability of pathogenic bacteria to adhere to the intestinal epithelium, to have immunomodulatory effects and to assist in the maintenance of well-being. Such bacteria are sometimes called probiotics and it has already been proposed to add suitable probiotic bacteria to infant formulas.

Extensive studies have been carried out to identify new probiotic strains. For example, EP 0 199 535, EP 0 768 375, WO 97/00078, EP 0 577 903 and WO 00/53200 disclose specific strains of *Lactobacilli* and *Bifidobacteria* and their beneficial effects.

As indicated above, by reason of their abilities to colonise the intestinal mucosa and reduce the capacity of pathogenic bacteria to adhere to the intestinal epithelium, certain probiotic strains have already been proposed for the prevention and treatment of diarrhoea in infants. For example, *Lactobacillus rhamnosus* ATCC 53103 which is sold inter alia by Valio Oy of Finland under the trade mark LGG has been reported to be effective in reducing bacterially-induced diarrhoea in infants and young children (Canani et al, British Medical Journal 2007, August 18;335 (7615):340). commonly added to human foods, such as fermented milk products.

Another approach to preventing or treating infection of the gastrointestinal tract with bacterial pathogens such as *Escherichia coli* (EPEC) is the administration of prebiotics, for example by addition to foodstuffs. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS). Shoaf et al. investigated the ability of various prebiotics including fructooligosaccharides, inulin, galacto-oligosaccharides, lactulose and raffinose to inhibit the attachment of EPEC strain E2348/69 on Hep-2 and Caco-2 cells. They observed that purified galacto-oligosaccharides exhibited the greatest adherence inhibition on both HEp-2 and Caco-2 cells, reducing the adherence of EPEC by 65 and 70%, respectively and concluded that their observations suggested that some prebiotic oligosaccharides may have anti-adhesive activity and directly inhibit the adherence of pathogens to the host epithelial cell surface (Infect Immun 2006 December;74 (12): 6920-8).

Human milk is known to contain a larger amount of indigestible oligosaccharides than most other animal milks. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are very resistant to enzymatic hydrolysis, indicating that these oligosaccharides may display essential functions not directly related to their calorific value.

As the composition of human milk becomes better understood, it has also been proposed to add prebiotics to infant formula. Various infant formulas supplemented with prebiotics such as mixtures of fructooligosaccharides and galactooligosaccharides for example are commercially available. However, such mixtures approximate only roughly the mixture of oligosaccharides in human milk. Over 100 different oligosaccharide components have been detected in human milk some of which have not been so far detected in animal milks such as bovine milk at all or have been detected only in small quantities. Examples of classes of human milk oligosaccharide that are present in bovine milk and colostrum only in very small quantities or not at all are sialylated and fucosylated oligosaccharides.

The number and function of these various oligosaccharides are still being elucidated although certain of them have also been associated with reducing the ability of pathogens to adhere to host epithelial cells. For example, Cravioto et al reported that an oligosaccharide-enriched fraction from human milk inhibited the attachment of EPEC to HEp-2 cells (The Journal of Infectious Diseases 1991; 163:1247-1255).

Infant formulas containing both probiotics and prebiotics have also been proposed in the continual quest to produce infant formulas which replicate as closely as possible the composition and efficacy of human milk. For example, in WO 2007/101675 it is proposed to supplement infant formula with a mixture of a probiotic bacterial strain and a mixture of N-acetylated, neutral and sialylated oligosaccharides which mixture provides a closer approximation to the oligosaccharides in human milk than does the commercially available mixtures of fructo- and galacto-oligosaccharides described above. It is stated that this mixture, which is described as a symbiotic, is useful for the prevention of pathogenic infections.

However, there is a continuing need to still further improve the protective effects of infant formulas and the like compositions by combining specific probiotics and prebiotics with particularly beneficial effects.

SUMMARY

It has now surprisingly been found that administration of N-acetyl-lactosamine and/or oligosaccharides containing N-acetyl-lactosamine is highly efficacious in enhancing the beneficial effects and efficiency of probiotic *Lactobacillus* sp co-administered with the oligosaccharide.

Accordingly, in a first aspect, the present invention provides a preparation comprising N-acetyl-lactosamine and/or an oligosaccharide containing N-acetyl-lactosamine and a probiotic *Lactobacillus* sp.

In a second aspect, the present invention provides the use of a probiotic *Lactobacillus* sp and N-acetyl-lactosamine and/or an oligosaccharide containing N-acetyl-lactosamine in the manufacture of a medicament or nutritional composition for the prevention and/or treatment of pathogenic infections of the gastro-intestinal tract.

The invention extends to a method for the prevention or treatment of pathogenic infections of the gastro-intestinal tract in a subject in need thereof which comprises administering to the subject a therapeutic amount of a preparation comprising a probiotic bacterial strain and a probiotic *Lactobacillus* sp and N-acetyl-lactosamine and/or an oligosaccharide containing N-acetyl-lactosamine.

The present inventors have previously demonstrated that a mixture of N-acetylated, neutral and sialylated oligosaccharides obtained from cows' milk is effective to stimulate *Lactobacillus rhamnosus* CGMCC 1.3724 to alleviate bacterial toxin induced damage and that the observed protection depends on bacterial-host cell crosstalk which is mediated in the presence of the OS blend (unpublished data). Without wishing to be bound by theory, the present inventors believe that the effectiveness of a combination of N-acetyl-lactosamine and/or an oligosaccharide containing N-acetyl-lactosamine with a probiotic *Lactobacillus* in the prevention or treatment of pathogenic infections of the respiratory and gastrointestinal tracts is due to a synergistic reduction in the ability of the pathogen to adhere to the luminal epithelium by the direct effect of the oligosaccharide on the bundle forming pili adhesins and other adhesins (e.g. intimin) and the indirect effect of the stimulated host-probiotic *Lactobacillus* crosstalk.

Additional features and advantages are described herein, and will be apparent from the following Detailed Description.

DETAILED DESCRIPTION

In the present specification, the following words are given a definition that must be taken into account when reading and interpreting the description, examples and claims:

"infant" means a child under the age of 12 months;

"infant formula" means a foodstuff intended for the complete nutrition of infants during the first four to six months of life and as a complement to other foodstuffs up to the age of 12 months;

"probiotic bacteria" means microbial cell preparations or components of microbial cells with a beneficial effect on the health or well-being of the host. (Salminen S, Ouwehand A. Benno Y. et al "Probiotics: how should they be defined" Trend Food Sci. Technol. 1999:10 107-10);

The invention relates to N-acetyl-lactosamine and/or an oligosaccharide containing N-acetyl-lactosamine. Suitable oligosaccharides containing N-acetyl-lactosamine include lacto-N-tetraose (LNT) and lacto-N-neotetraose (LNnT). LNT and LNnT may be synthesised chemically by enzymatic transfer of saccharide units from donor moieties to acceptor moieties using glycosyltransferases as described for example in U.S. Pat. No. 5,288,637. Alternatively, LNT and LNnT may be prepared by chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828. N-acetyllactosamine produced in this way may then be transferred to lactose as acceptor moiety.

The probiotic *Lactobacillus* may be selected from any *Lactobacillus* strain which satisfies the definition of a probiotic and has acceptable shelf-life for the product into which the preparation of the invention is to be incorporated. For example, infant formulas are required to remain stable and effective for up to 36 months. Of course, the preparation of the invention does not need to be incorporated into another product such as a foodstuff but may be ingested as is or mixed with a suitable excipient in the form of a powder or capsule or compressed into tablets for example.

Examples of preferred *Lactobacillus* species are *Lactobacillus rhamnosus*, *Lactobacillus paracasei* and *Lactobacillus reuteri*. Particularly preferred strains are *Lactobacillus rhamnosus* ATCC 53103, *Lactobacillus rhamnosus* CGMCC 1.3724, *Lactobacillus reuteri* ATCC 55730 and *Lactobacillus reuteri* DSM 17938.

The selected probiotic *Lactobacillus* may be cultured according to any suitable method known in the art and prepared for addition to the preparation or nutritional composition of the invention by freeze-drying or spray-drying for example. Alternatively, bacterial strains can be bought from specialist suppliers such as Christian Hansen and Morinaga already prepared in a suitable form for addition to nutritional compositions such as infant formula.

The preparation of the invention may provide between $10^2$ and $10^{10}$ cfu of probiotic bacteria for each gram of the oligosaccharide.

In a preferred aspect of the invention, the preparation described above is incorporated into a nutritional composition. In the context of the present invention, the term "nutritional composition" is intended to encompass any consumable matter. Hence, it may be a product intended for consumption by humans, in particular infant formula, growing up milk, and the like. However, consumption of the preparation is not restricted to infants and children In particular, the preparation of the invention can be incorporated into dehydrated milk or cereal mixtures.

The nutritional composition is preferably an infant formula which contains N-acetyl-lactosamine and/or an oligosaccharide containing N-acetyl-lactosamine in an amount between 0.1 and 3 g/100 g composition on a dry weight basis.

An infant formula according to the present invention may contain a protein source in an amount of not more than 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The infant formula may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

The infant formula may contain a source of lipids. The lipid source may be any lipid or fat which is suitable for use in infant formulas. Preferred fat sources include palm olein, high oleic sunflower oil and high oleic safflower oil. The essential fatty acids linoleic and a-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

In addition to the N-acetyl-lactosamine and/or an oligosaccharide containing N-acetyl-lactosamine the infant formula preferably further contains at least one prebiotic in an amount of 0.3 to 10%. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®. A particularly preferred combination of prebiotics is a mixture comprising 5-70 wt % of at least one N-acetylated oligosaccharide selected from the group comprising GalNAcα1,3Galβ1,4Glc and Galβ1,6GalNAcα1,3Galβ1,4Glc, 20-95 wt % of at least one neutral oligosaccharide selected from the group comprising Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc and Galβ1,3Galβ1,3Galβ1,4Glc and 2-50 wt % of at least one sialylated oligosaccharide selected from the group comprising NeuAcα2,3Galβ1,4Glc and NeuAcα2,6Galβ1,4Glc. Such a mixture may be prepared from an animal milk as described for example in WO2007/101675.

The infant formula may optionally contain other substances which may have a beneficial effect such as lactoferrin, nucleotides, nucleosides, and the like.

If the preparation of the invention is to be incorporated in an infant formula or other milk-based nutritional composition, the composition may be prepared in any suitable manner known in the art. For example, an infant formula may be prepared by blending together the protein source, any carbohydrates other than lactose and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then be cooled to about 60° C. to about 85° C., for example by flash cooling. The liquid mixture may then be homogenised, for example in two stages at about 7 MPa to about 40 MPa in the first stage and about 2 MPa to about 14 MPa in the second stage. The homogenised mixture may then be further cooled to add any heat sensitive components such as vitamins and minerals. The pH and solids content of the homogenised mixture is conveniently standardised at this point.

The homogenised mixture is transferred to a suitable drying apparatus, such as a spray drier or freeze drier, and converted to powder. The powder should have a moisture content of less than about 5% by weight.

The preparation of the invention may be made up in advance and added directly to nutritional composition by dry mixing. Alternatively, the probiotic *Lactobacillus* and the N-acetyl-lactosamine and/or oligosaccharide containing N-acetyl-lactosamine may be added separately to the nutritional composition by dry mixing.

In another embodiment, the preparation of the invention may be in the form of a supplement including the probiotic *Lactobacillus* and the N-acetyl-lactosamine and/or an oligosaccharide containing N-acetyl-lactosamine in an amount sufficient to achieve the desired effect in an individual. Preferably the daily dose of the N-acetyl-lactosamine and/or oligosaccharide containing N-acetyl-lactosamine is from 0.1 to 3 g and the daily dose of the probiotic *Lactobacillus* is from 10e5 to 10e12 cfu. The amounts of N-acetyl-lactosamine and/or oligosaccharide containing N-acetyl-lactosamine and probiotic *Lactobacillus* to be included in the supplement will be selected accordingly depending upon how the supplement is to be administered. For example, if the supplement is to be administered twice a day, each supplement may contain 0.05 to 1.5 g N-acetyl-lactosamine and/or oligosaccharide containing N-acetyl-lactosamine and 10e3 to 10e6 cfu of probiotic *Lactobacillus*. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or enteral administration as well as vitamins, minerals trace elements and other micronutrients in accordance with the recommendations of Government bodies such as the USRDA.

A preparation according to the invention is particularly effective in the prevention and treatment of pathogenic infections of the upper respiratory and gastrointestinal tracts including by enteropathogenic *E. coli* (EPEC), enterohaemorhagic *E. coli* (EHEC) enterotoxigenic *E. coli* (ETEC) and *Salmonella* sp as regards infections of the gastrointestinal tract and by *Streptococcus pneumoniae* as regards infections of the upper respiratory tract.

The invention will now be further illustrated by reference to the following example.

EXAMPLE 1

An example of the composition of a suitable infant formula to be used in the present invention is given below

| Nutrient | per 100 kcal | per liter |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |

-continued

| Nutrient | per 100 kcal | per liter |
| --- | --- | --- |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| LNnT (mg) | 37 | 250 |
| *L. rhamnosus* CGMCC 1.3724 | $2.10^7$ cfu/g of powder, live bacteria | |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for treatment of a pathogenic infection of the upper respiratory tract, the method comprising administering to an individual in need thereof a composition comprising a probiotic *Lactobacillus* sp and a component selected from the group consisting of N-acetyl-lactosamine and an oligosaccharide containing N-acetyl-lactosamine, wherein the composition is administered to the individual in an amount that provides 0.1 to 3 g of the component per day and $10^5$ to $10^{12}$ cfu of the probiotic *Lactobacillus* sp per day, the probiotic *Lactobacillus* sp is present in the composition in an amount between $10^2$ and $10^{10}$ cfu for each gram of the component.

2. The method of claim 1 wherein the infection is caused by pathogenic bacteria.

3. The method of claim 1 wherein the probiotic *Lactobacillus* sp is selected from the group consisting of *Lactobacillus rhamnosus* ATCC 53103, *Lactobacillus rhamnosus* CGMCC 1.3724, *Lactobacillus reuteri* ATCC 55730 and *Lactobacillus reuteri* DSM 17938.

4. The method of claim 1 wherein the component is lacto-N-neotetraose.

5. The method of claim 1 wherein the composition comprises 1.8 to 2.0 g of protein/100 kcal of the composition.

6. A method for treatment of otitis media, the method comprising administering to an individual in need thereof a composition comprising a probiotic *Lactobacillus* sp and a component selected from the group consisting of N-acetyl-lactosamine and an oligosaccharide containing N-acetyl-lactosamine, wherein the composition is administered to the individual in an amount that provides 0.1 to 3 g of the component per day and $10^5$ to $10^{12}$ cfu of the probiotic *Lactobacillus* sp per day, the probiotic *Lactobacillus* sp is present in the composition in an amount between $10^2$ and $10^{10}$ cfu for each gram of the component.

7. The method of claim 6 wherein the otitis media is caused by pathogenic bacteria.

8. The method of claim 6 wherein the probiotic *Lactobacillus* sp is selected from the group consisting of *Lactobacillus rhamnosus* ATCC 53103, *Lactobacillus rhamnosus* CGMCC 1.3724, *Lactobacillus reuteri* ATCC 55730 and *Lactobacillus reuteri* DSM 17938.

9. The method of claim 6 wherein the component is lacto-N-neotetraose.

10. The method of claim 6 wherein the composition comprises 1.8 to 2.0 g of protein/100 kcal of the composition.

\* \* \* \* \*